(12) United States Patent
Chiesa et al.

(10) Patent No.: US 7,938,117 B2
(45) Date of Patent: *May 10, 2011

(54) RESPIRATORY MASK

(75) Inventors: Paul Chiesa, Candia, NH (US); Doug Park, Windham, NH (US)

(73) Assignee: SleepNet Corporation, Hampton, NH (US)

( * ) Notice: Subject to any disclaimer, the term of this patent is extended or adjusted under 35 U.S.C. 154(b) by 1039 days.

This patent is subject to a terminal disclaimer.

(21) Appl. No.: 11/607,791

(22) Filed: Dec. 1, 2006

(65) Prior Publication Data

US 2007/0101997 A1 May 10, 2007

Related U.S. Application Data

(63) Continuation-in-part of application No. 09/979,972, filed on Nov. 28, 2001, now Pat. No. 7,210,481.

(60) Provisional application No. 60/741,304, filed on Dec. 1, 2005.

(51) Int. Cl.
*A62B 18/02* (2006.01)

(52) U.S. Cl. .......... 128/205.25; 128/206.24; 128/207.18
(58) Field of Classification Search .......... 128/201.22–201.24, 204.18, 205.25, 128/205.27–207.18
See application file for complete search history.

(56) References Cited

U.S. PATENT DOCUMENTS

| | | | | |
|---|---|---|---|---|
| 5,003,633 A | * | 4/1991 | Itoh | 2/9 |
| 5,429,683 A | | 7/1995 | Le Mitouard | |
| 5,647,357 A | | 7/1997 | Barnett et al. | |
| 5,655,527 A | * | 8/1997 | Scarberry et al. | 128/206.24 |
| 6,615,832 B1 | * | 9/2003 | Chen | 128/206.26 |
| 2005/0284479 A1 | * | 12/2005 | Schrader et al. | 128/205.25 |

OTHER PUBLICATIONS

EPO, International Search Report, Mar. 19, 2007.

* cited by examiner

*Primary Examiner* — Steven O Douglas
(74) *Attorney, Agent, or Firm* — Holland & Bonzagni, P.C.; Donald S. Holland, Esq.

(57) ABSTRACT

The present invention is a system for stiffening a portion of the perimeter of a respiratory mask that has a formable element disposed about its perimeter, thereby making the respiratory mask more comfortable to wear.

9 Claims, 3 Drawing Sheets

RESPIRATORY MASK

CROSS-REFERENCE TO RELATED APPLICATIONS

The present application claims the benefit of U.S. Provisional Application Ser. No. 60/741,304 filed Dec. 1, 2005, which is incorporated herein by reference, and is a continuation-in-part of U.S. Utility patent application Ser. No. 09/979,972 filed Nov. 28, 2001, now U.S. Pat. No. 7,210,481, issued May 1, 2007.

TECHNICAL FIELD

This invention relates to a respiratory mask used to supply a breathable gas to a patient. More specifically, it relates to a better means to conform such a mask, whether it is a nasal or full-face respiratory mask (hereinafter, collectively, "masks"), to the portions of a patient's face that the mask contacts.

BACKGROUND OF THE INVENTION

A number of relatively common breathing disorders are treated by delivery of pressurized, breathable gas to a patient's airway. This is customarily done through the use of a mask. A mask is normally held in place over a patient's nose or face by one or more straps. The straps encircle the patient's head and are adjusted to create a gas tight seal between the mask and the patient's face. For example, as shown in FIG. 1, a nasal mask 10 includes a shell 12, forming a chamber with a seal 18. The seal 18 contacts the wearer's face forming the gas tight seal.

The patient's nasal area and face are complexly contoured and differ from patient to patient. Thus, during extended use, the mask may move relative to the patient's nose or face breaking the gas tight seal or becoming uncomfortable. The customary response is for the patient to tighten the mask's straps, which may cause the mask to push too strongly on the soft tissue surrounding the patient's nose or on the patient's face.

FIG. 2 shows an example of how this problem was addressed in the prior art. As is described in more detail in U.S. patent application Ser. No. 09/979,972 filed Nov. 28, 2001, the constructed of a compliant and resilient material. Disposed along the perimeter 24, and only the perimeter 24 of the shell is a formable element 26. The formable element may be a wire made for a relatively soft metal such as aluminum or copper or other materials known to those skilled in the art. The formable element may be affixed to the surface of the shell or molded within the shell.

The formable element 26 can be constructed from any material that is formable and is capable of retaining the shape into which it is formed against the force of, for example, the resilient shell 22 trying to regain its memory shape. The combination of the compliant and resilient shell 22 and the formable element 26, having sufficient rigidity to hold the shell 22 in a selected configuration, produces a "custom-fit" as desired by a particular user. Because the shell 22 is compliant, the perimeter and overall configuration of the shell 22 can be reformed repeatedly, as necessary, by a particular user.

In use, this mask, as shown in FIG. 3, tends to crease along a midline C running from the point 32 at which the mask contacts the bridge of the patient's nose to the point 33 at which the mask contacts the patient's face in the middle of the patient's chin. This crease causes the mask to become uncomfortable and causes the gas tight seal to be broken.

SUMMARY OF THE INVENTION

The present invention relates to a respiratory mask that is more comfortable to wear and conforms better to a wearer's face. It is a system for stiffening one or more portions of a formable element disposed around the perimeter of the respiratory mask.

BRIEF DESCRIPTION OF THE DRAWINGS

These and other features and advantages of the present invention will be better understood by reading the following detailed description, taken together with the drawings wherein preferred embodiments are shown as follows.

DETAILED DESCRIPTION OF THE INVENTION

Figures 1, 2:
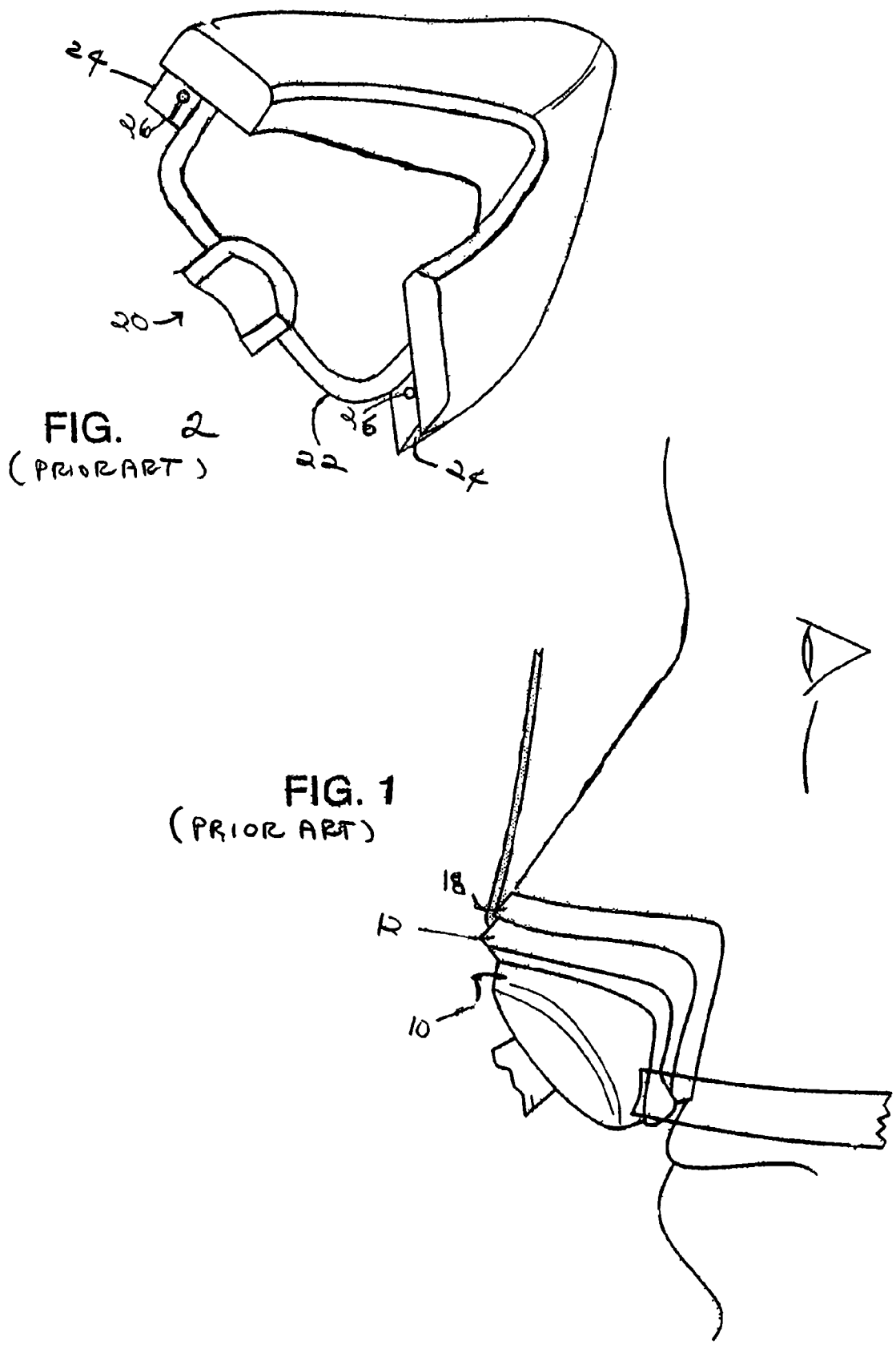
FIG. 1 shows a nasal mask of the prior art in use.
FIG. 2 shows a schematic cross section of a full-face mask of the prior art.
Figure 3:
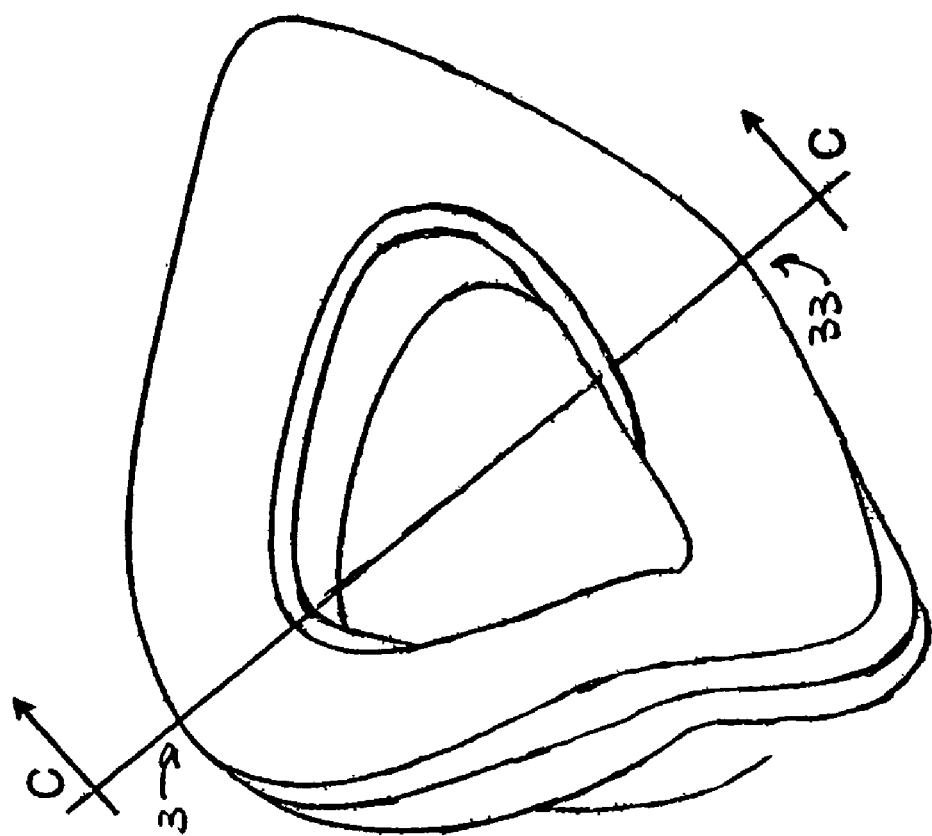
FIG. 3 shows a schematic perspective view of a full-face mask of the prior art.
Figure 4:
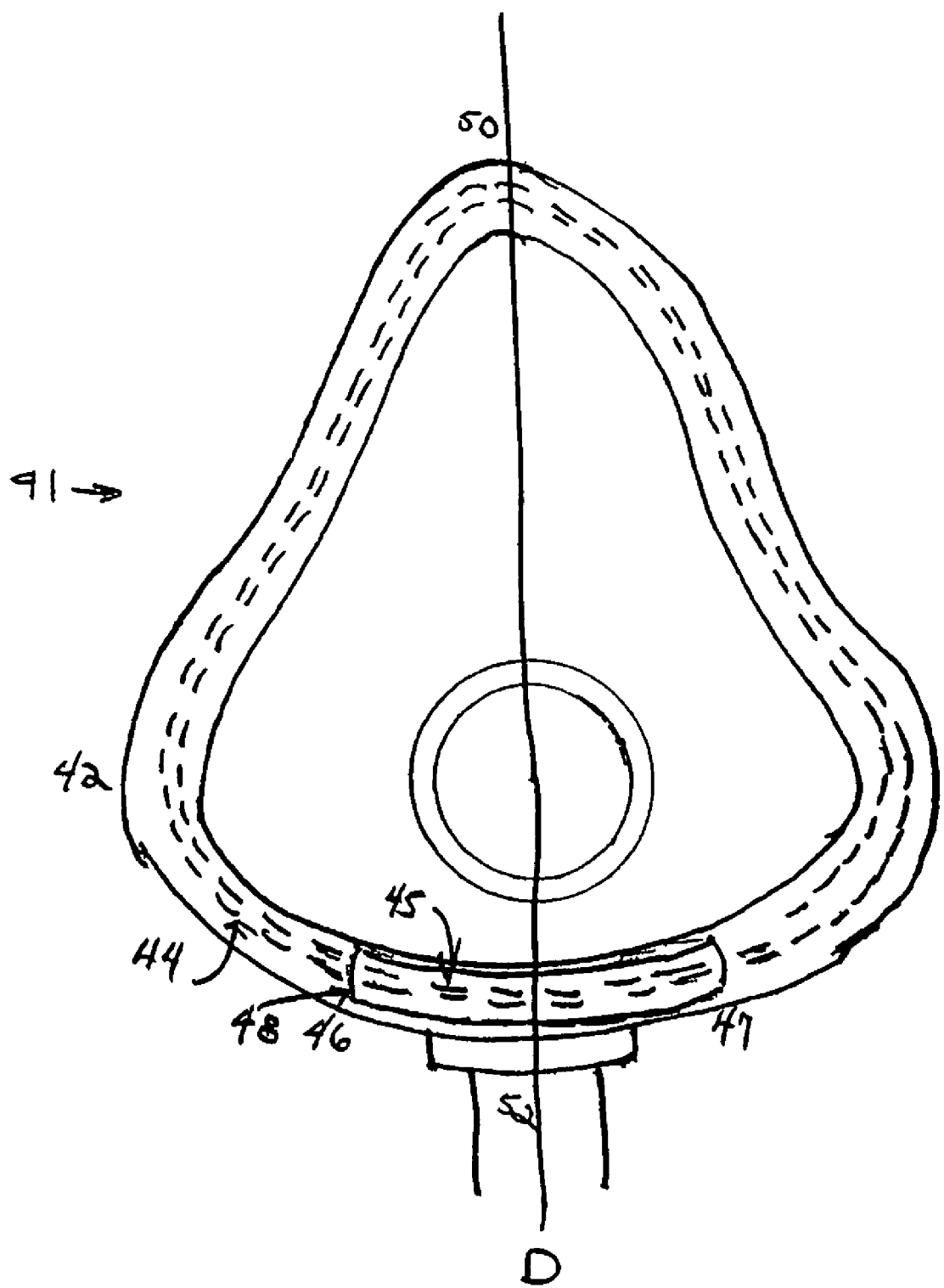
FIG. 4 shows a schematic perspective view of a preferred embodiment of the present invention.

The present invention provides a system for stiffening, as described in more detail herein, a portion of the perimeter of a mask that has a formable element disposed about its perimeter. Referring to FIG. 4, one preferred embodiment of a full face mask 41 has a shell 42 constructed of a compliant and resilient material. A formable element 44 is disposed along the perimeter, and only the perimeter, of the shell 42. The formable element 44 can be affixed to the surface of the shell 42 but is molded within the shell 42 here. A portion 45 of the formable element 44 running along the wearer's chin from 46 to 47 is stiffened. It is stiffened in this preferred embodiment by molding a polycarbonate sleeve 48 over the portion 45 of the formable element 44 before the formable element 44, and polycarbonate sleeve 48, are molded in the shell 42. This causes the portion 45 of the formable element 44 to become more difficult to bend but not to be rigid, i.e., to be stiffened, compared to the remainder of the formable element 44. The shell 42 of the mask 41 will not crease along the mid-line D running from point 50 at which the mask contacts the bridge of the patient's nose to point 52 at which the mask contacts the patient's face in the middle of the patient's chin as prior art masks might. In other preferred embodiments, one or more other portions of the formable element 44 may be stiffened to eliminate creasing or bending in such other portions.

It should be noted that there are a number of means known to those skilled in the art to stiffen a portion of the formable element 42. A polycarbonate overmold is one of the least costly and most esthetically attractive. It should also be noted that the portion 45 of the formable element 44 that is stiffened should have some "give" in it. If it is made rigid, the formable element 44 tends to fail at points 46 and 47.

The formable element 44 can be constructed from any suitable material that is malleable and is capable of retaining the shape into which it is formed against the force of, for example, the compliant shell 42 trying to regain its memory shape. The combination of the compliant shell 42, malleable element 44 and stiffener (e.g., 48) produces sufficient rigidity to hold the shell 42 in a selected "custom-fit" configuration, formed by a particular user or wearer. Because the shell 42 is compliant, the perimeter and overall configuration of an opening of the shell can be reformed repeatedly, as necessary, by the user or wearer of mask 41.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention.

What is claimed is:

1. A full face respiratory mask for providing breathable gas to a wearer, the mask comprising:
   a. a shell forming a chamber having an inlet and an outlet with a perimeter;
   b. a malleable element disposed around the entirety of the perimeter and only around said perimeter, the malleable element being formable and capable of holding the perimeter of the shell in a custom fit configuration, formed by the wearer, to produce a desired fit;
   c. a stiffener for at least one portion of the malleable element; and
   d. a seal disposed proximate the outlet, the seal dimensioned and shaped to contact the seal with external skin around two nares at a base of a nose of the wearer, wherein substantially all of the sealing occurs between the seal and the external skin; and
   e. wherein the custom fit configuration of the perimeter of the shell is retained after the mask is worn.

2. The respiratory mask of claim 1 wherein the stiffener runs along a chin of the wearer.

3. The respiratory mask of claim 1 wherein the malleable element comprises a wire made of relatively soft metal.

4. The respiratory mask of claim 1 wherein the malleable element is disposed within the shell.

5. The respiratory mask of claim 1 wherein the stiffener is a molded polycarbonate sleeve which covers the at least one portion of the malleable element.

6. The respiratory mask of claim 1 wherein the seal comprises a bladder.

7. The respiratory mask of claim 6 wherein the bladder is filled with silicone gel.

8. The respiratory mask of claim 7 wherein the gel is molded in a predetermined configuration.

9. The respiratory mask of claim 1 wherein the seal is bonded to the shell.

* * * * *